(12) United States Patent
Majewski (10) Patent No.: US 7,732,774 B2
(45) Date of Patent: Jun. 8, 2010

(54) HIGH RESOLUTION PET BREAST IMAGER WITH IMPROVED DETECTION EFFICIENCY

(75) Inventor: Stanislaw Majewski, Yorktown, VA (US)

(73) Assignee: Jefferson Science Associates, LLC, Newport News, VA (US)

( * ) Notice: Subject to any disclaimer, the term of this patent is extended or adjusted under 35 U.S.C. 154(b) by 92 days.

(21) Appl. No.: 12/284,287

(22) Filed: Sep. 19, 2008

(65) Prior Publication Data

US 2010/0074399 A1    Mar. 25, 2010

(51) Int. Cl.
G01T 1/164 (2006.01)
(52) U.S. Cl. .................................. 250/363.04
(58) Field of Classification Search ............ 250/363.04; 378/37
See application file for complete search history.

(56) References Cited

U.S. PATENT DOCUMENTS

| | | | | |
|---|---|---|---|---|
| 4,733,083 | A  * | 3/1988  | Wong | 250/363.03 |
| 6,242,743 | B1 * | 6/2001  | DeVito et al. | 250/363.05 |
| 6,744,053 | B2 * | 6/2004  | Wong et al. | 250/394 |
| 6,946,841 | B2 * | 9/2005  | Rubashov | 324/318 |
| 7,102,135 | B2 * | 9/2006  | Lecoq | 250/363.03 |
| 7,205,546 | B1 * | 4/2007  | Kennedy | 250/363.02 |
| 2003/0233110 | A1 * | 12/2003 | Jesseph | 606/167 |
| 2004/0026620 | A1 * | 2/2004  | Peter et al. | 250/309 |
| 2004/0081273 | A1 * | 4/2004  | Ning | 378/37 |
| 2008/0077005 | A1 * | 3/2008  | Piron et al. | 600/411 |
| 2008/0103391 | A1 * | 5/2008  | Dos Santos Varela | 600/436 |
| 2008/0208044 | A1 * | 8/2008  | Lecoq et al. | 600/436 |

OTHER PUBLICATIONS

Karimian et al., "A Cylindrical PET System for Breast Imaging", Nuclear Instruments and Methods in Physics Research, A 545 (2005) pp. 427-435.
Proffitt et al., "A Flexible High-Rate USB2 Data Acquisition System for PET and SPECT Imaging", IEEE Nuclear Science Symposium Conference Record, Puerto Rico, Oct. 23-29, 2005, pp. 2971-2975.
Proffitt et al., "Implementation of a High-Rate USB Data Acquisition System for PET and SPECT Imaging", IEEE Nuclear Science Symposium Conference Record, San Diego, California, Oct. 29-Nov. 1, 2006, pp. 3063-3067.
Raylman et. al., "Development of a Dedicated Positron Emission Tomography System for the Detection and Biopsy of Breast Cancer", MIMA, 2006, 564(2): pp. 291-295.

* cited by examiner

Primary Examiner—David P Porta
Assistant Examiner—Marcus H Taningco (57) ABSTRACT

A highly efficient PET breast imager for detecting lesions in the entire breast including those located close to the patient's chest wall. The breast imager includes a ring of imaging modules surrounding the imaged breast. Each imaging module includes a slant imaging light guide inserted between a gamma radiation sensor and a photodetector. The slant light guide permits the gamma radiation sensors to be placed in close proximity to the skin of the chest wall thereby extending the sensitive region of the imager to the base of the breast. Several types of photodetectors are proposed for use in the detector modules, with compact silicon photomultipliers as the preferred choice, due to its high compactness. The geometry of the detector heads and the arrangement of the detector ring significantly reduce dead regions thereby improving detection efficiency for lesions located close to the chest wall.

18 Claims, 8 Drawing Sheets

HIGH RESOLUTION PET BREAST IMAGER WITH IMPROVED DETECTION EFFICIENCY

The United States of America may have certain rights to this invention under Management and Operating contract No. DE-AC05-06OR23177 from the Department of Energy.

FIELD OF THE INVENTION

This invention relates to breast imaging and more particularly to a high resolution PET breast imaging system with improved detection efficiency for lesions located close to the chest wall of a patient.

BACKGROUND OF THE INVENTION

Breast cancer biology seems to indicate that breast cancer metastasis starts at the lesion size of about 2 mm. While X-ray mammography offers much better intrinsic spatial resolution, on the order of 50 micrometers, this anatomical imaging modality suffers from poor specificity to the type (cancerous or benign, etc.) of the suspicious structure seen on the mammogram. In some patients this X-ray imaging technique is not useful at all due to dense breast tissue, implants, or scars as the result of previously performed surgery. Breast MRI can provide more structural information than mammography but it also provides nonspecific information about the type of tissue imaged. Imaging techniques offering information as to the type or biology of the anatomical structures present in the breast and especially any suspicious lesions are based on biomarkers sensitive to molecular species present in the tissue. Examples of these functional or molecular imagers are Positron Emission Tomography (PET) scanners and gamma cameras. These standard imaging instruments are not capable of achieving spatial resolution in breast at the range of 2 mm or better, as is desirable, as mentioned above. It is therefore crucial to develop functional imaging techniques that can produce imaging power on the 1 mm resolution scale.

Although there has been proposed breast-specific functional imagers including dedicated compact gamma cameras placed close to breast, physical limits are imposed on their resolution by the parallel-hole mechanical collimator and the effect of distance between the imaged feature to the surface of the collimator. Radiotracer used in single gamma breast imaging with standard gamma cameras and with specialized breast-specific instruments is typically Tc-99m-Sestamibi, labeled with Tc99m, which emits gamma rays at 140 keV. Typically, the best average linear spatial resolution obtained in a compressed breast with these instruments using parallel-hole collimators is on the order of 5-6 mm. A partial remedy to this problem is imaging the compressed breast simultaneously from both sides, therefore reducing the average distance from any feature in the volume of the breast to the nearest collimator. However, even in this case the 2 mm limit is practically not obtainable due to interrelation between the collimator resolution and sensitivity. While parallel collimators offering 2 mm spatial resolution at a 2.5 cm distance can be made available, their sensitivity will be too low and the resulting images will exhibit too much statistical noise to allow efficient detection of small cancerous lesions. Other imaging schemes with pinhole collimators were proposed to attain better spatial resolution, but they still suffer from poor sensitivity due to the function of the pinhole gamma collimator.

FDA-approved dedicated breast PET imagers are available from Naviscan PET Systems of San Diego, Calif. These instruments are capable of achieving spatial resolution of <2 mm FWHM with F-18 positron-emitting radiolabels used for example in the F-18-fluorodeoxyglucose (FDG) biomarker. However, they suffer from another problem, related to the physics process of coincidence PET coincidence imaging, which results in poor sensitivity in the region of the breast close to chest wall. PET detection efficiency drops quickly off at the detector edges because of the geometrical requirement of simultaneous detection of two back to back 511 keV annihilation gamma rays produced in the act of positron annihilation with one of the electrons of the surrounding breast tissue. This produces a dead edge or sharp drop in detection efficiency when approaching the edge plane of the system. In comparison, single photon imaging does not suffer to the same extent from the chest wall effect and in addition one can use for example the slant collimator solution that will further reduce the dead region effect. This geometrical effect was defined in a recent clinical trial study as the cause of missing lesions placed at the base of the breast, close to the wall chest region. It is therefore a serious limitation and recognized deficiency of the dedicated PET breast imaging procedure as currently implemented with planar scanning modules.

Another example of a prior art breast imaging PET system is that described by RR Raylman, et al. in Development of a Dedicated Positron Emission Tomography System for the Detection and Biopsy of Breast Cancer, *NIMA*, 2006; 564(2): 291-295. The imaging system includes two pairs of planar PET imager modules mounted on a rotating gantry under a patient's bed. The two pairs of modules in this proposed system have only limited reach towards the patient's chest wall and therefore, are unable to image the breast region closest to the chest wall.

SUMMARY OF THE INVENTION

A method and apparatus is proposed to remedy the problem associated with dedicated PET breast imagers of missing lesions placed in the region of the breast close to the patient's chest wall. The highly efficient breast imager includes a ring of detection modules surrounding the imaged breast. A slant imaging light guide is inserted between the gamma radiation scintillator sensor and the photodetector in each imaging module. The slant light guide element permits the gamma sensors to be placed in very close proximity to the skin of the chest wall, thereby extending the sensitive region of the imager to the base of the breast. Several types of photodetectors are proposed for use in the detector modules, with the new so called compact silicon photomultiplier as the preferred choice, due to its high compactness.

OBJECTS AND ADVANTAGES

Several advantages are achieved with the breast imager of the present invention, including:

(1) The breast imager is built from imager modules each having a slant optical fiberoptic light guide inserted between the scintillator sensor and the photodetector, permitting placement of the scintillation sensors very close to the chest wall, almost touching the patient's skin.

(2) The breast imager is arranged in the form of a ring and the ring is imbedded in a properly shaped patient bed to enable positioning the edge of the detection modules directly at the chest wall.

(3) The geometry of the detector heads and the arrangement of the detector ring significantly reduce dead regions between individual detector heads as compared to conventional PET systems, therefore permitting static imaging.

(4) The detector ring is mounted on a disk attached to a scanning system that permits limited angle rotation around the breast and vertical scanning toward and away from the chest wall to enable whole breast imaging.

These and other objects and advantages of the present invention will be better understood by reading the following description along with reference to the drawings.

INDEX TO REFERENCE NUMERALS IN DRAWINGS 20 breast imager
22 photodetector module
24 breast
26 chest wall
28 patient bed
30 scintillator sensor
32 Position Sensitive Photo Multiplier Tube (PSPMT)
34 optical lightguide
36 plane defining the top edge of the photodetector module
38 top edge of the photodetector module
39 readout
40 breast imager
42 scanner ring
44 portion of patient's bed
46 photodetector module or imager module
47 patient bed
48 inner tube
49 directional arrow
50 breast imaging system, first embodiment
60 breast imaging system, second embodiment
62 top imaging ring
64 bottom imaging ring
66 PMT perimeter
68 gap
70 breast imaging system, second embodiment
71 ring of imaging modules
72 imaging module
73 thin wall tube
74 scintillator sensor
75 fiberoptic lightguide
76 optical window
77 PMT enclosure
78 breast imaging system, third embodiment
79A first imaging ring sector
79B second imaging ring sector
80 side port
81 scintillator module
82 round PMT
84 scintillator block
86 fiberoptic light guide
88 scintillator block
90 major silicon imaging module or photodetector
92 basic silicon imaging module
94 3 mm basic silicon unit or pad
95 readout channel comprised of four pads
96 readout channel comprised of sixteen pads
97 one inch square silicon photodetector
98 dead region
100 small-size detector module using silicon MPPCs
102 silicon MPPC
104 scintillator array
106 slant fiberoptic light guide
108 silicon PMT array

DETAILED DESCRIPTION OF THE INVENTION

Figure 1:
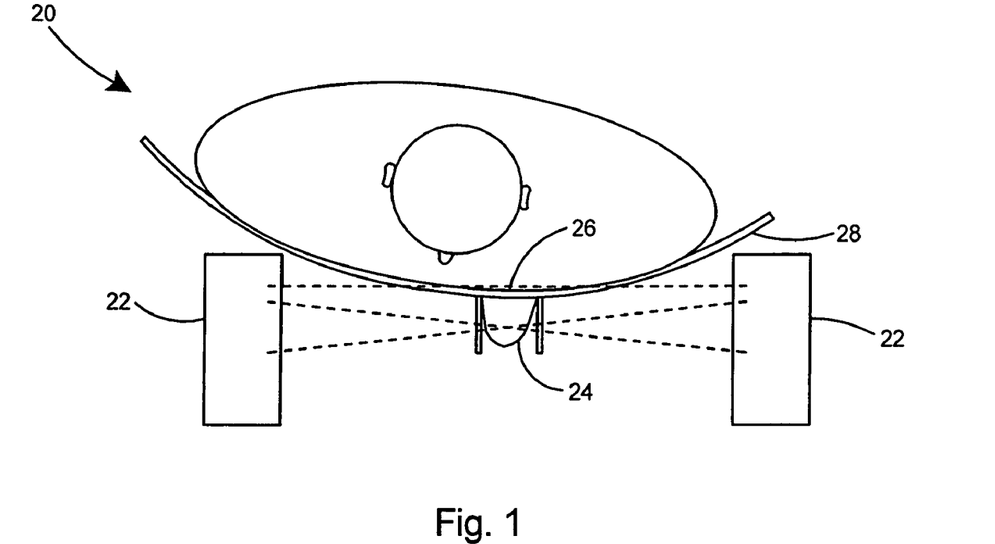
FIG. 1 is an end view of one version of a breast imaging system according to the present invention including a set of detector modules viewing the breast in a lateral position and with the detector heads raised past the edge of the chest wall to permit efficient detection of lesions in the breast region close to the chest wall.

With reference to FIG. 1 there is shown a first embodiment of a breast imaging system 20 according to the present invention including a set of photodetector modules 22 viewing the breast 24 in a lateral position and with the detector heads raised past the edge of the chest wall 26 to permit efficient detection of lesions in the breast region close to the chest wall. The imaging system includes lateral imaging geometry with the detector heads 22 put further apart with one or two detector heads 22 raised past the edge of the chest wall 26 to permit efficient detection of lesions in the breast region close to the chest wall 26. The light-weight patient bed 28, which is preferably constructed of hard plastic or a carbon-fiber matrix, has a shape approximating a fraction of a cylinder to facilitate placement of the detector heads 22 higher than the chest wall 26.

Figure 2:
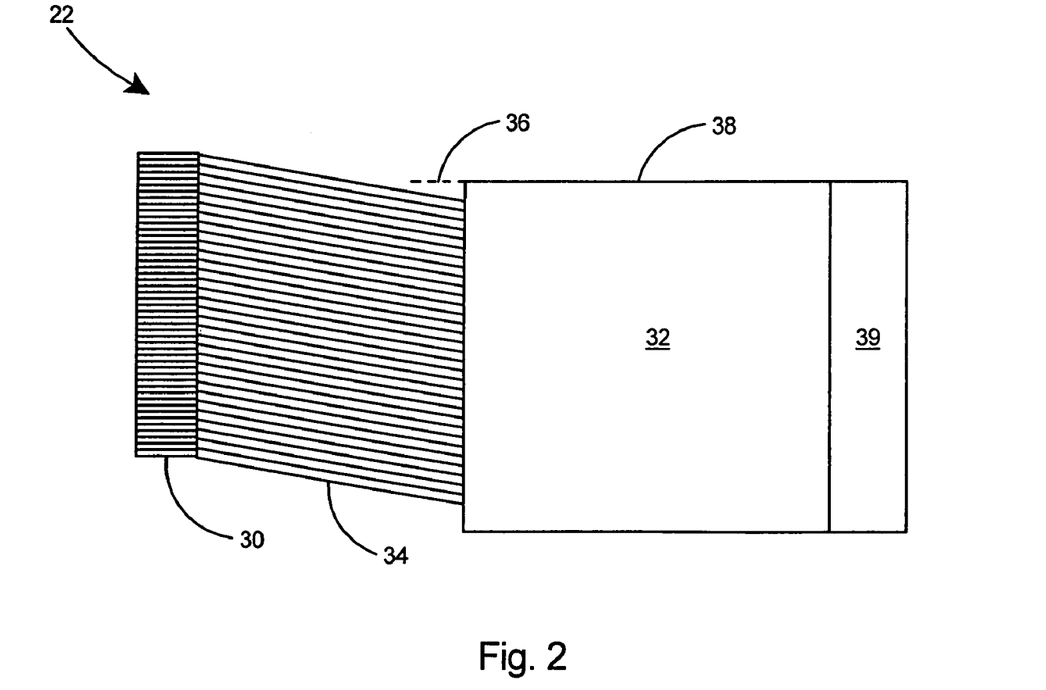
FIG. 2 is a side view of a preferred imaging module according to the present invention including a scintillator array coupled to a Position Sensitive PMT via an optical lightguide made of an array of arranged plastic fibers.

The second and preferred embodiment of the imaging system of the present invention includes a ring of detection modules surrounding the imaged breast and is designed to minimize edge dead space. With reference to FIG. 2 there is shown an imaging or detector module 22 based on a scintillator array 30 coupled to a Position Sensitive PMT 32 via an optical lightguide 34 that is constructed of an array of arranged plastic fibers. The slant shape of the light guide 34 allows for the edge of the scintillation sensor element 30 to be placed above the plane 36 defining the top edge 38 of the photodetector module 22. In this way the sensor module 30 is protruding towards the chest wall of the patient. The slant imaging light guide 34 is inserted between the gamma radiation sensor or scintillator 30 and the photodetector 32 in each imaging module 22. The slant light guide 34 permits the gamma sensors 30 to be placed almost directly by the skin of the chest wall (see FIG. 3) and therefore they extend the sensitive region of the imager to the base of the breast. Preferably, the slant imaging light guide 34 is a multi-fiber light guide that includes a slant angle of between 5 and 45 degrees and a most preferred slant angle of 10 degrees. An electronic readout 39 is provided at one end of the PMT 32.

Figure 3:
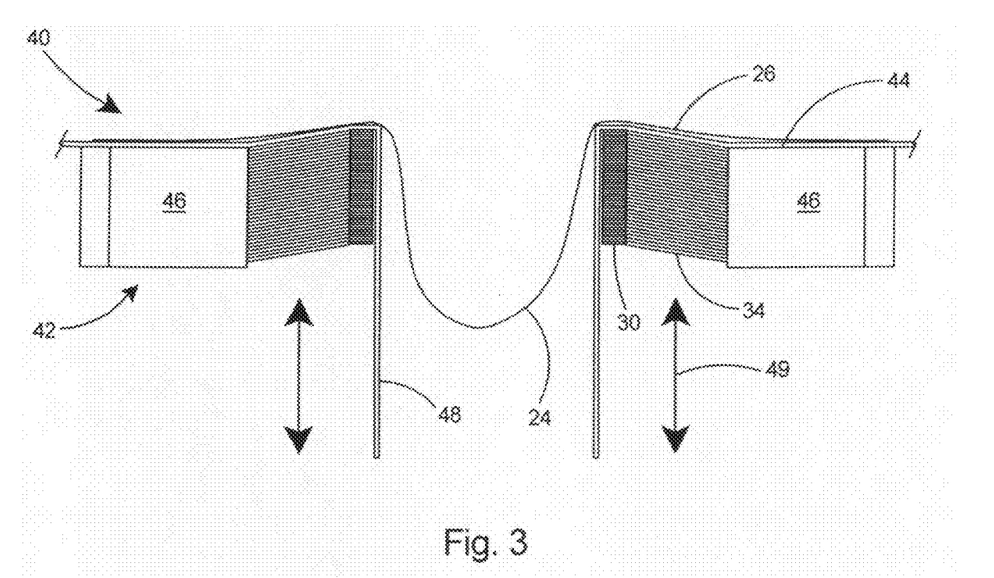
FIG. 3 is a cross-sectional view through an imager ring and part of the patient's bed depicting the imager modules thrust against the chest wall.

Referring to the imaging system or breast imager 40 in FIG. 3 there is shown a cross-sectional view through an imager or scanner ring 42 and a portion of the patient's bed 44 depicting the placement of the imager modules 46 such that they will be thrust against the chest wall 26 of the patient. The shaped bed 44, the inner tube 48, and side housing (not shown) will enclose the scanner ring 42. Within the enclosure the scanner ring 42 can be rotated by small angles and scanned up and down, as indicated by directional arrows 49, to provide sufficient coverage and angular sampling of the imaged breast 24 by the photodetector modules 46. The patient bed 44 is preferably constructed of thin composite material or plastic. The patient bed 44 includes cushioning on top for patient comfort. Cushioning at the edges of the inner tube 48 is shaped to enable close positioning of the thin imager ring 42 to the chest wall 26. Alternatively, as shown in FIG. 4, a conventional table 47 may be used with the breast imaging system of the current invention, such as the table used in core-biopsy procedures that is available from Lorad Corporation, Danbury, Conn.

Figure 4:
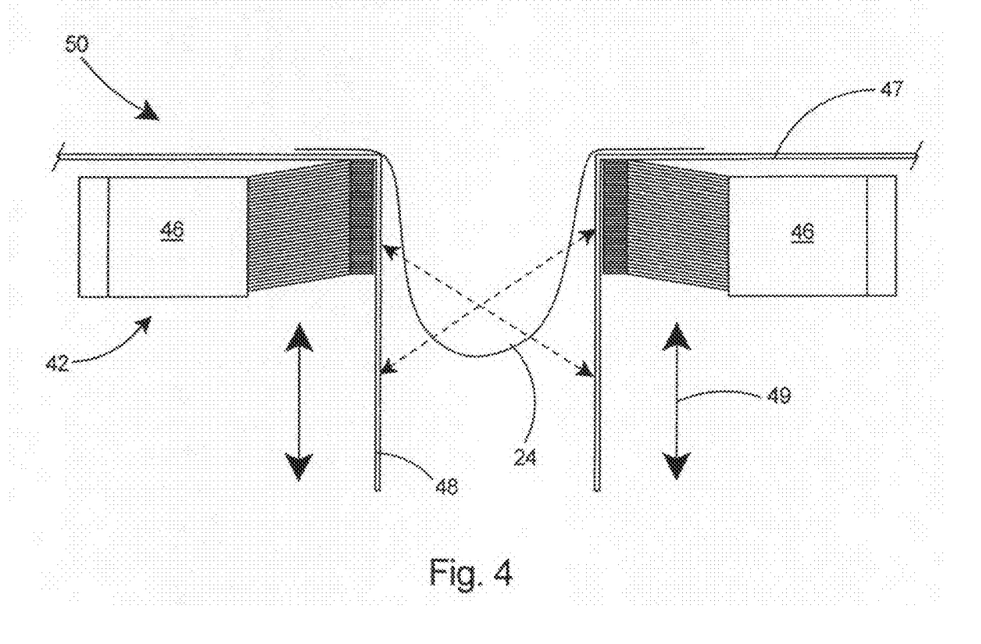
FIG. 4 is a sectional view of an imaging system according to the present invention with the pendant breast of a patient inserted in a tube portion of a patient bed with a circle of imaging modules surrounding the tube.

With reference to FIG. 4 there is shown a first embodiment of a breast imaging system 50 according to the present invention. The patient is in a prone position with the pendant breast 24 inserted in the cylindrical thin wall tube 48 with a circle of imaging modules 46 surrounding the tube 48. In this embodiment of the breast imaging system 50, one ring 42 of photodetector modules 46 is provided, and the ring 42 can be scanned or moved in the vertical axis along directional lines 49 to scan the whole volume of the breast 24. The photodetector modules 46 can be rotated slightly around the thin wall tube 48.

Figure 5:
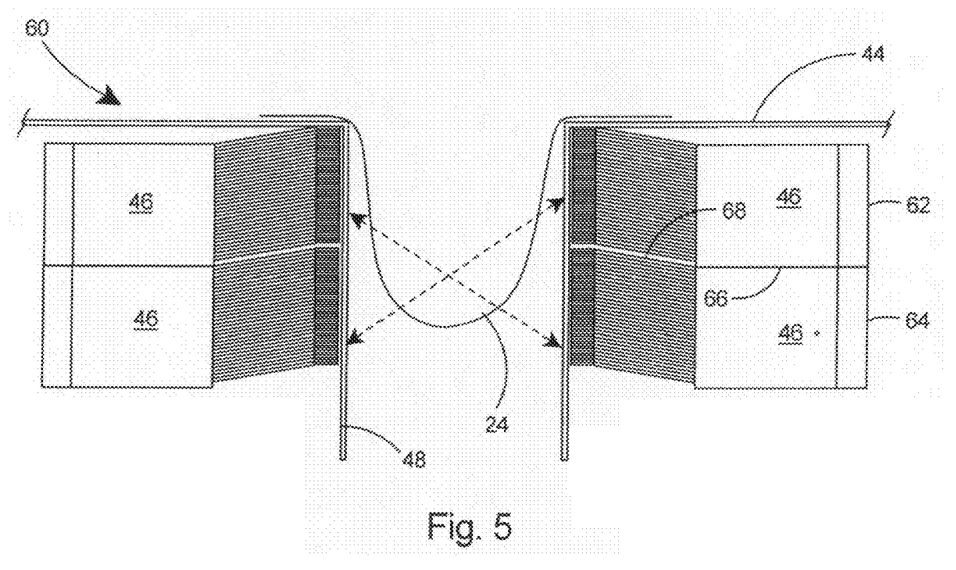
FIG. 5 is a side view of an imaging system according to the present invention including two rings of imaging modules.

A second embodiment of the breast imaging system 60 is depicted in FIG. 5. In the embodiment depicted in FIG. 5, two rings of imaging modules 46 are provided, including a top imaging ring 62 and a bottom imaging ring 64, and the whole set of imaging rings 62 and 64 can be moved vertically to cover the whole volume of the breast 24. In this particular embodiment the dead edge at the PMT perimeter 66 results in a small physical gap 68 between the two imaging rings 62 and 64. The impact of the gap 68 is minimal on the final quality of the reconstructed images. If desired, additional detector rings could be added to create a breast imaging system with three or more rings (not shown) to eliminate the need for vertical scanning and cover the whole breast volume without requiring movement of the detector rings.

In the breast imaging systems of the present invention, the breast to be imaged will be pending through the inner tube 48 in the patient bed 44 as shown in FIG. 5. An alternative embodiment for the imaging procedure would include compression of the breast, especially when immobilizing the breast for image guided biopsy. Several arrangements are available for breast immobilization, including placing the breast in a plastic container or bag and applying sub-atmospheric pressure with a small pressure differential. The pressure differential would be produced by a low power pump. An alternative arrangement for breast immobilization would include a vacuum pump for fixing the pendulous breast in the center of the field of view (FOV) as proposed by Karimian et al., "CYBPET: a cylindrical PET system for breast imaging", Nuclear Instruments and Methods in Physics Research A 545 (2005) 427-435. In that example an approximate 20 cm port diameter, which is suitable for almost all adult female breast sizes, surrounds an individual pendulous breast which is under mildly reduced pressure within a thin flexible plastic membrane.

Figure 6A:
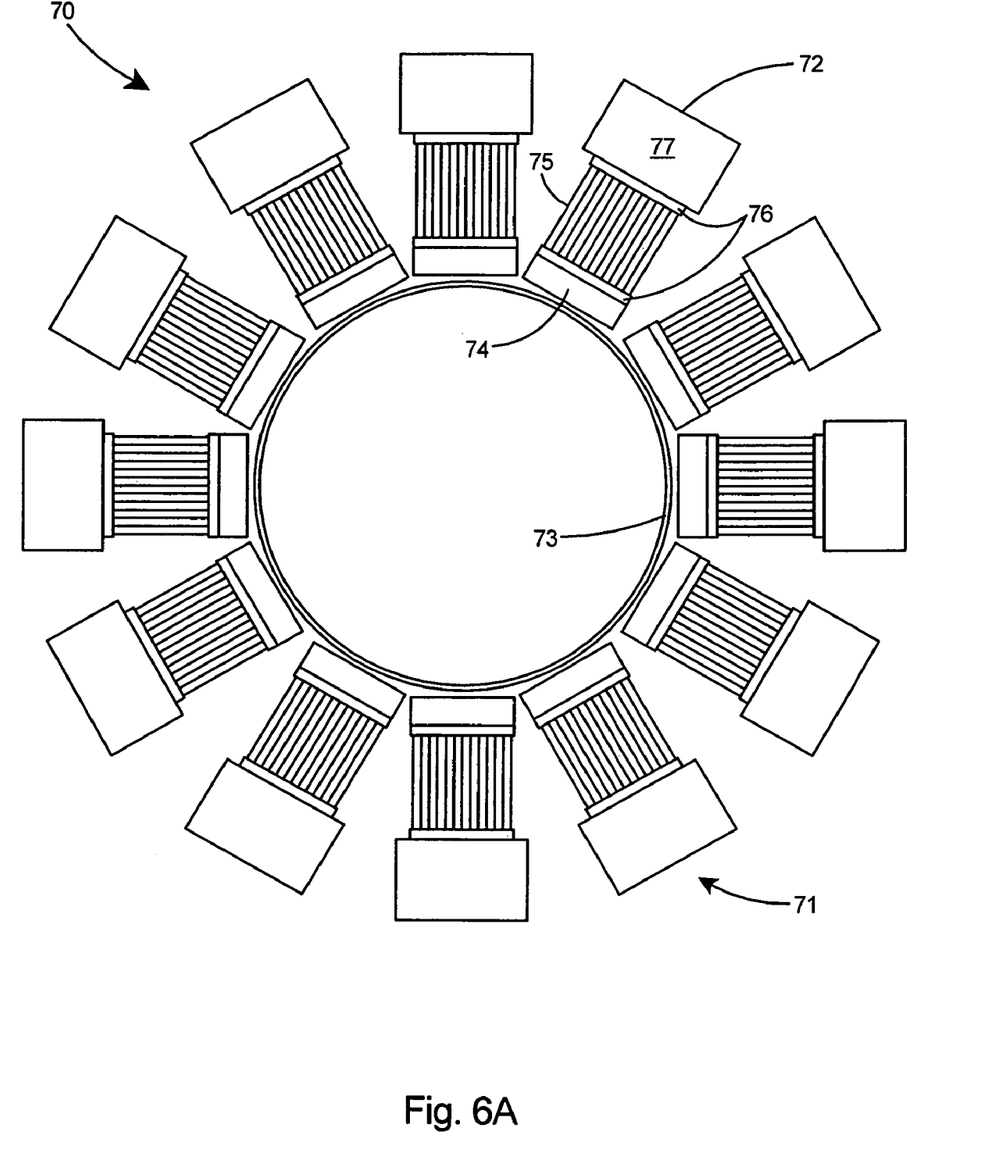
FIG. 6A is a top view of an imaging system according to the present invention that includes a ring of imaging detectors surrounding a thin wall tube in which the ring of detectors can be scanned or moved along the vertical axis to scan the whole volume of the breast and can be rotated slightly around the thin wall tube to provide all the necessary angular views for 3D tomographic reconstruction.

With reference to FIG. 6A there is shown a top view of the second and preferred embodiment of an imaging system 70 according to the present invention. The breast imaging system 70 includes a ring 71 of imaging modules 72 surrounding a thin wall tube 73 in which a breast (not shown) is positioned. Each imaging module 72 includes a scintillator sensor 74, a fiberoptic lightguide 75, optical windows 76 on either end of the lightguide 75, and a PMT enclosure 77 that includes the PMT and associated electronics.

Figure 6B:
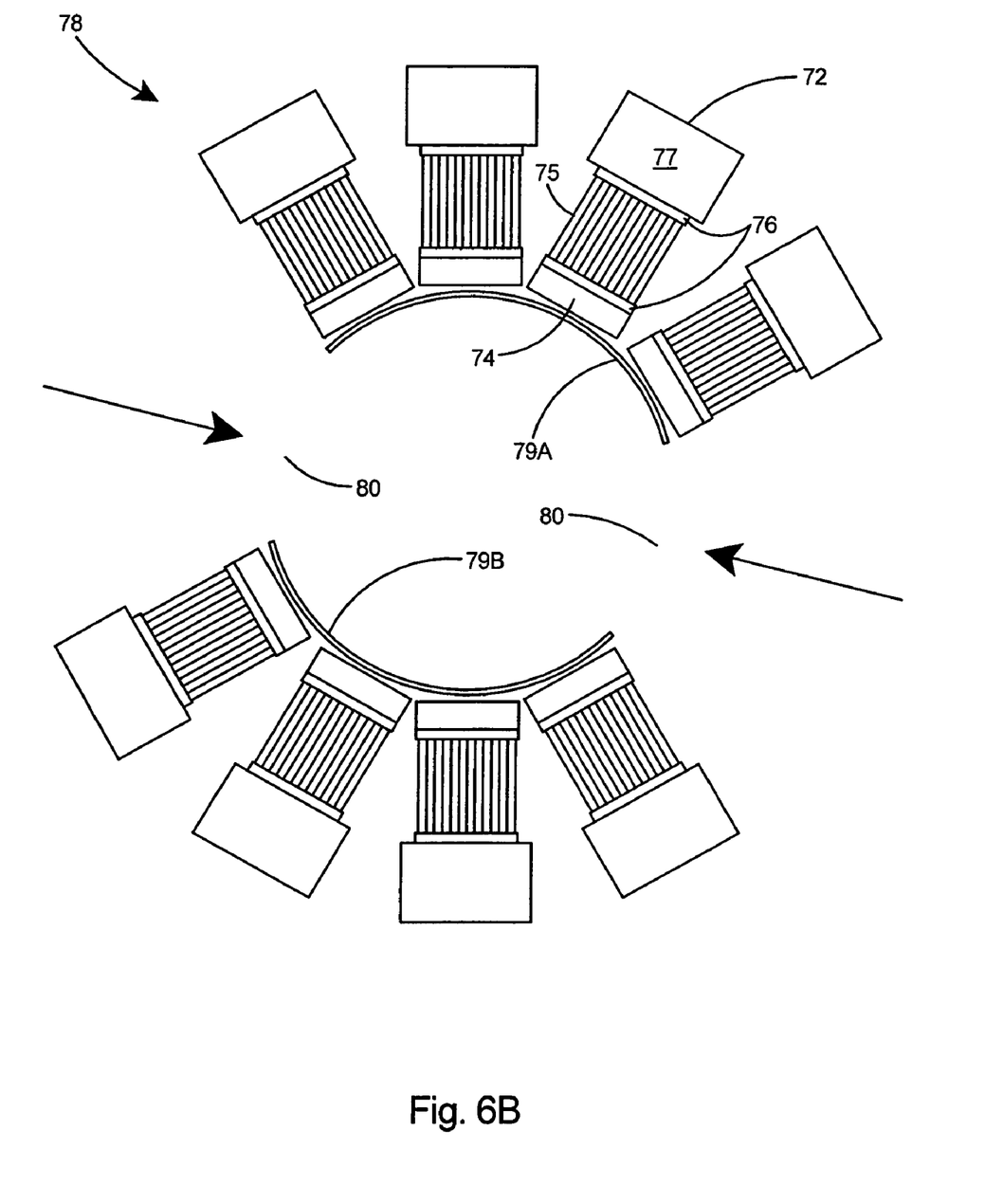
FIG. 6B is a top view of an imaging system according to the present invention that includes two ring sectors in which the detectors are rotated around the breast to provide all the necessary angular views for 3D tomographic reconstruction.

FIG. 6B depicts a top view of a third embodiment of an imaging system 78 similar to the imaging system of FIG. 6A but in which the imaging modules 72 are in two imaging ring sectors 79A and 79B. The imaging modules 72 are rotated around the breast (not shown) to provide all the angular views that are necessary for 3D tomographic reconstruction. This embodiment of the breast imager 78 is an economical arrangement composed of two imaging ring sectors 79A and 79B only. This embodiment of the breast imager 78 offers convenient side ports 80 for installing a biopsy device. The imager 78 provides the convenience of performing the biopsy procedure while imaging the breast. By using a radioactive tip biopsy needle (not shown), the needle tip is guided to the lesion by the imaging system 78.

Referring to FIG. 2, a dedicated breast PET imager according to the present invention could include several imaging technologies. The preferred general type of a solution will have a scintillator sensor 30 as a sensor/energy converter of the 511 keV annihilation gamma rays, while different photodetectors 32 can serve as detectors of the scintillation light produced by the absorbed 511 keV gamma rays in the scintillator gamma sensor 30. The scintillator sensor 30 can be made from plate or from pixelated array crystal scintillator materials. Most preferably, the scintillator sensor 30 is constructed from pixelated high stopping power crystal scintillator materials such as LSO, LYSO, LuAP, LFS, GSO, GYSO, BGO, NaI(Tl), or LaBr3. The photodetector 32 may be a standard or multi-element photomultiplier or a position sensitive, flat panel or microchannel plate based photomultiplier. Alternatively, the photodetector 32 may be an avalanche photodiode array or large size avalanche photodiodes with resistive readouts. As another alternative, the photodetector 32 may be a silicon photomultiplier. Examples of commercially available flat panel photomultipliers are models H8500 or H9500 from Hamamatsu Corporation of Bridgewater, N.J., or several models from the 85000 series, available from Photonis USA, Inc. of Sturbridge, Mass. These position sensitive photomultipliers each have an active surface area of approximately 5 cm×5 cm.

An alternative more economical solution for the basic detection module 22 of the outside detector heads, can be based on multi-element PMTs such as small-profile 2" square nine-element XP1470 PMTs available from Photonis USA, Inc. However, the achieved intrinsic spatial resolution may be only marginally satisfactory for 2 mm pitch scintillation pixels. Additionally, these PMTs are much slower than Hamamatsu H8500 flat panel PMTs, primarily due to time shifts between individual nine inner channels. A further disadvantage of a system built on the XP1470 PMTs is that it would be much more bulky.

Figure 7:
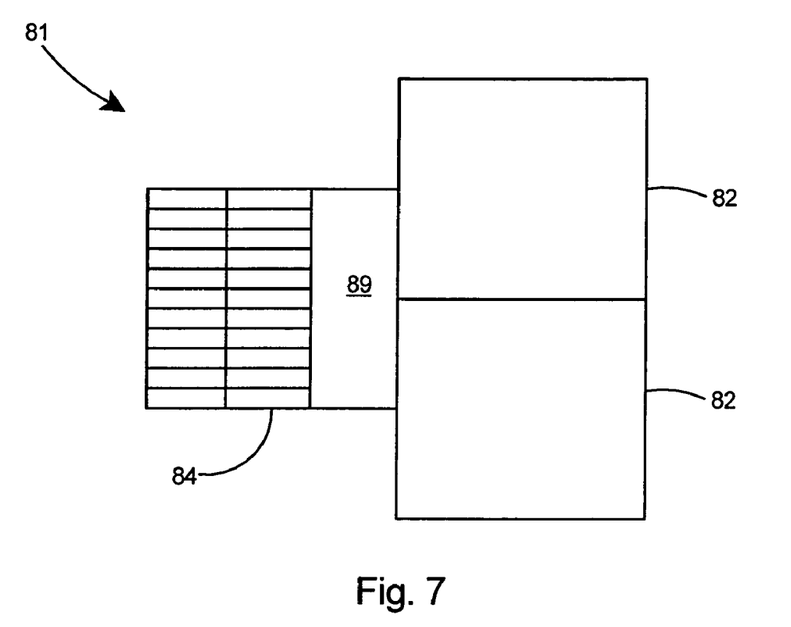
FIG. 7 is a sectional view of a scintillation module with an array of four standard square or round PMTs coupled in a standard direct coupling mode to a scintillator block.
Figure 8:
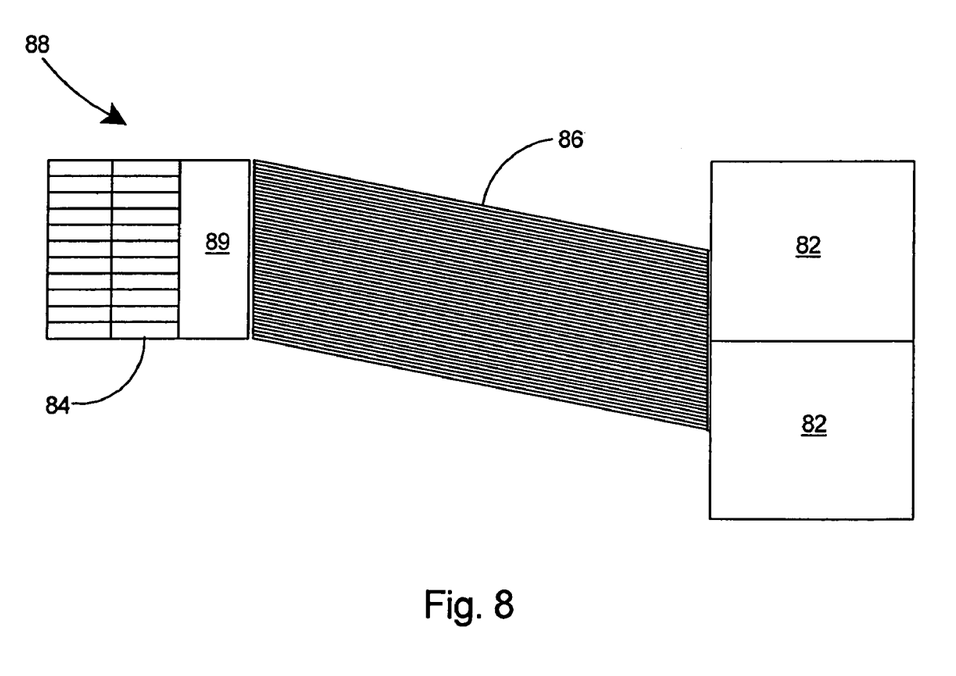
FIG. 8 is a sectional view depicting the application of a slant fiberoptic light guide applied to the four standard square or round PMTs of FIG. 7 to permit the use of the standard PMTs in a dedicated PET breast imager according to the present invention.

With reference to FIGS. 7 and 8, standard square or even round PMTs can be used to form an edgeless detector design according to the present invention. FIG. 7 is a sectional view of a scintillation module 81 with an array of 2×2 standard round PMTs 82 coupled in a standard direct coupling mode to a scintillator block 84. In this example the dead edge region, when used in standard direct coupling mode, is much larger than in the case of Position Sensitive PMTs. Nevertheless, application of a slant fiberoptic light guide 86 as shown in FIG. 8, creates a scintillator block 88 that can be used in a dedicated PET breast imager according to the present invention. FIG. 8 is a sectional view depicting the application of the slant fiberoptic light guide 86 applied to the four standard round PMTs 82 of FIG. 7 to permit the use of the round PMTs 82 in a dedicated PET breast imager according to the present invention. The two-layer phoswitch scintillator example is shown (taken from the Siemens high resolution brain PET HRRT detector module design) with two layers of 10 mm long and 2×2 mm scintillation pixels of LYSO on top and LSO at bottom, and a specially shaped light guide 89.

Slant light guides 86 according to the present invention can be constructed from different materials such as: glass, quartz, plastics including polystyrene, acrylic, polyvinyl toluene (PVT), or liquid core light guides. The light guide elements can be straight or bent in the range of sizes or diameters from 10 micron to 3 mm, depending on the material. Tight and regularly arranged arrays of these individual light guide elements or fibers form the slant light guides with transverse sizes matching the size of the photodetector module. For example in the case of H8500 or H9500 flat panel PMT, the size of approximately 52 mm square is desired. The length of the light guide 86 can be from few centimeters to 20 cm and more. In addition, between the scintillation element 84 and the light guide 86, as well as between the light guide 86 and the surface of the photodetector 82, optical windows 89 can be introduced to help accept, transmit and deliver the light signal in the array of fibers or other individual elements forming the light guide 86. For example in case of scintillation arrays such a window can help to spread scintillation light from each of the scintillation array pixels into more fibers to improve pixel-to-pixel light sampling uniformity, due to the quantized nature of both the scintillator 84 and the light guide 86. The preferred material of construction of the optical windows includes glass, quartz, and plastic. The fiberoptic windows can be either straight or tapered. The scintillation array 84 can include an outer light-tight window (not shown) constructed of approximately 1 mm thick aluminum or equivalent as a protection sheet or shell for light tightness and mechanical protection. Preferably a plastic or metal shell or box (not shown) with an opening in front of the scintillation array 84 will be used to house the detector modules. In a breast imager according to the present invention the entire ring of modules, such as rings 62 and 64 in FIG. 5, will be protected by a thin outer skin (not shown) and built into the patient bed.

With reference to FIG. 3, a specific embodiment for a high resolution breast imaging system with improved detection efficiency for lesions located close to the chest wall of a patient includes a ring 42 of individual detection modules, each based on a Hamamatsu H8500 flat panel PMT 46 coupled to an array 34 of 24×24 LYSO 2×2×15 mm pixels with a 2.1 mm pitch. Each module 46 has four analog position outputs and one fast energy output. The position outputs are recorded and digitized in the DAQ system to calculate position of the interacting 511 keV gamma ray. The fast sum signal is used to create the coincident event triggers in the trigger electronics, provided then to the DAQ system to record the event data from the detector modules. The optimal on-board readout design will include PMT gain uniformity correction assuring high energy and spatial resolutions and high rate performance with minimal number of readout channels.

Figure 9:
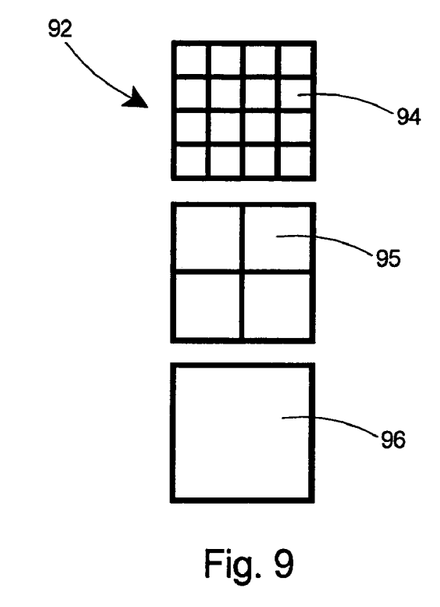
FIG. 9 depicts a basic initial 12.5 mm silicon PMT imaging module constructed of an array of sixteen 3 mm×3 mm readout pixels or pads arranged in a 4×4 array.
Figure 10:
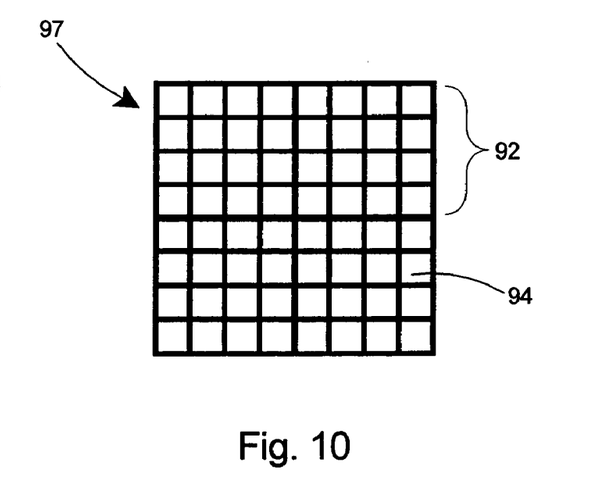
FIG. 10 depicts an array of 2×2 of the basic four-side buttable modules of FIG. 9 butted together to form an approximately one inch square photodetector.
Figure 11:
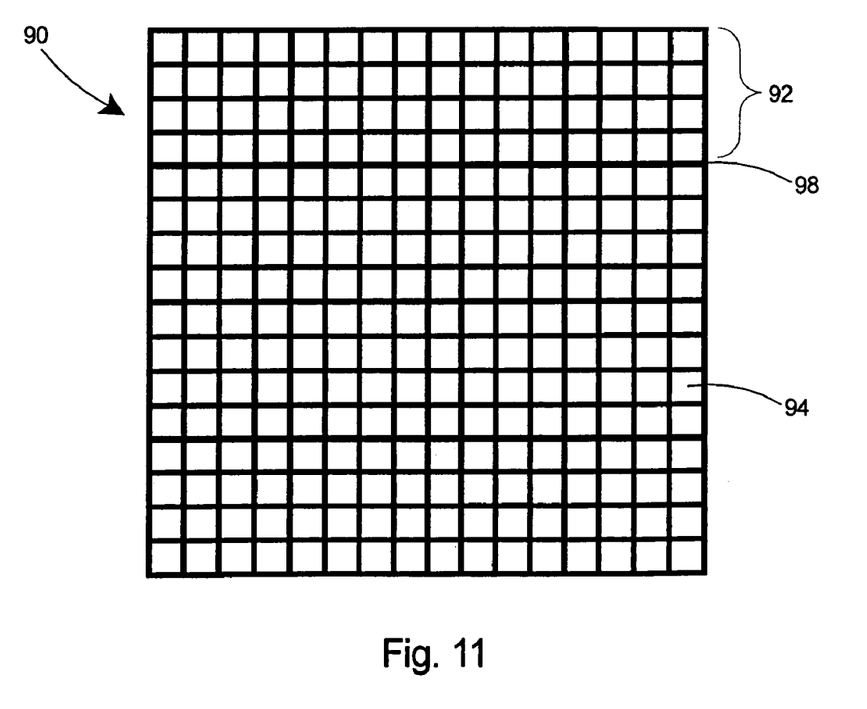
FIG. 11 depicts an even larger module that can be implemented by arranging 16 (in array of 4×4) basic imaging modules.

In a breast imager according to the present invention, silicon PMT is the preferred material for the photodetector and can be used in lieu of position sensitive PMTs. Typically, silicon PMT modules come in small units of about 3 mm in size. Arrays of these devices are therefore needed to cover the same active field of view. FIGS. 9-11 show an example of how to achieve a silicon PMT based photodetector 90 (FIG. 11) of approximately 5 cm×5 cm active field of view using nominal 12.5 mm silicon PMT basic imaging modules 92 (FIG. 9) each composed of sixteen 3 mm silicon PMT units 94. As shown in FIG. 9, the basic initial imaging module 92 can have an array of sixteen 3 mm×3 mm readout pixels or pads 94 arranged in a 4×4 array. The 3 mm pads or units 94 can be either read separately or with four pads 94 connected to one readout channel 95 or coarsely 96 with all 16 pads 94 connected to one readout channel 96, as shown schematically at center and bottom of FIG. 9, respectively. As shown in FIG. 10, an array of 2×2 of these basic four-sides buttable modules (made of 8×8=64 of 3 mm silicon PMT units) forms an approximately 1" square photodetector 97 equivalent for example to a commercially available Hamamatsu R8520-C12 PSPMT. The basic imaging modules 92 will be four-side buttable with an estimated 1 mm dead space at the edges. As shown in FIG. 11, the photodetector modules are preferably arranged in major imaging modules 90 composed of 4×4 basic modules 92, with coverage and readout needs equivalent to the H8500 or H9500 flat panel PMT discussed hereinabove. The major imaging module 90 can for example be used as a plug-in replacement module for the H8500/H9500 flat panel PMT with an approximate 5 cm×5 cm active surface. The dead regions 98 between the basic modules will be about 1-2 mm wide, which will enable adequate scintillation signal sampling for uniform energy and spatial response.

Figure 12:
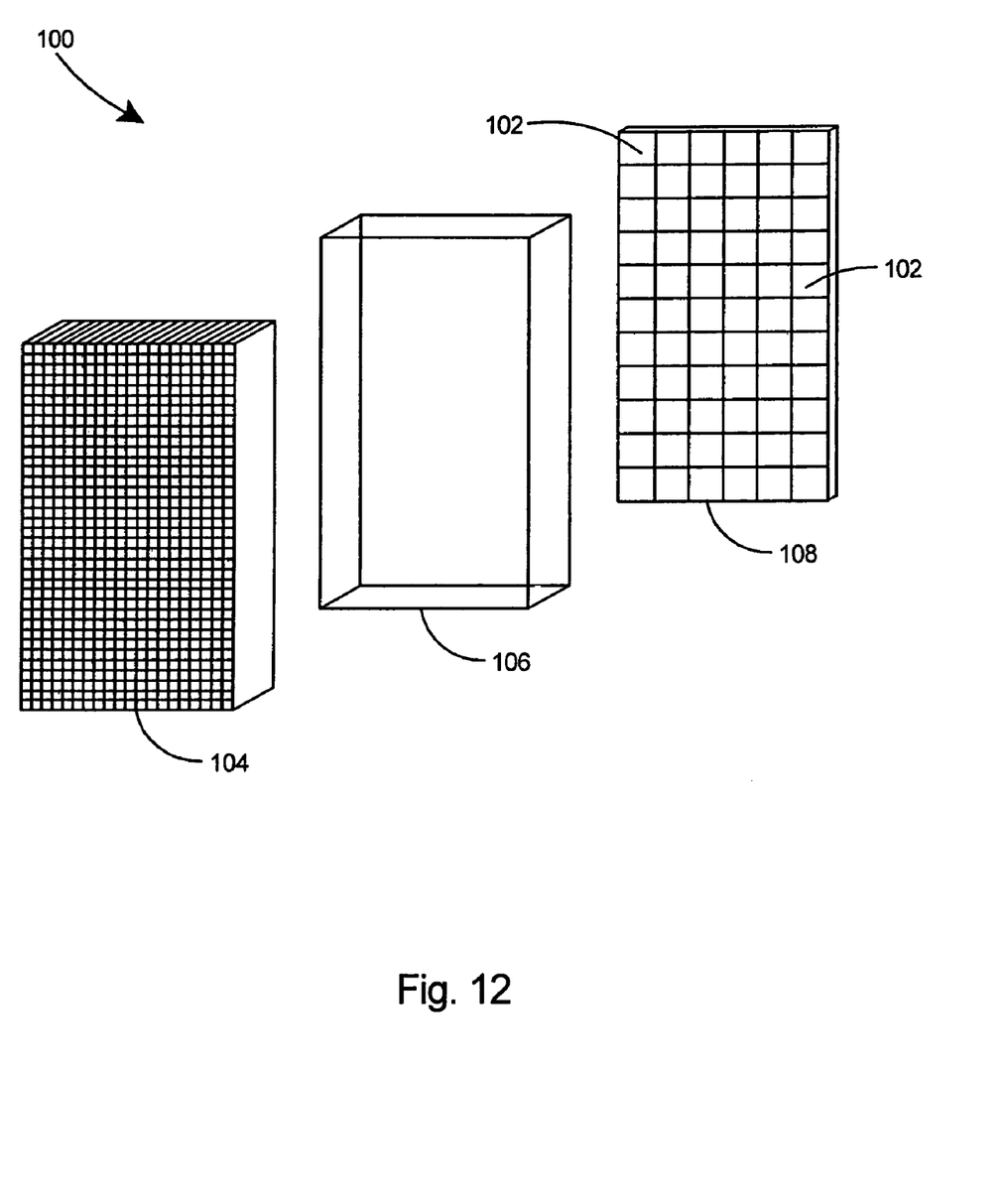
FIG. 12 is a perspective view of an imaging system according to the present invention including a small-size prototype detector module using commercially available detection elements to form an active field of view of over 2.5 cm wide by 5 cm high.

With reference to FIG. 12 there is shown a conceptual drawing of a detection module constructed according to the present invention with small silicon photomultiplier sensors. The sensors used in this example are the 3×3 mm-MPPC-SMD package from Hamamatsu. FIG. 12 is a schematic depicting the formation of a small-size detector module 100 using Hamamatsu S10362-33 silicon multi-pixel photon counters (MPPC) 102. The detection module includes a scintillator array 104, a slant fiberoptic light guide 106, and the silicon PMT array 108. Each detection element 102 occupies an approximate 5 mm square area in the array 108. In the example depicted in FIG. 12 an active field of view of over 2.5 cm (wide) by 5 cm (high) is covered by the 6×11 silicon PMT array 108, equivalent to a set of two R8520-C12 PSPMTs or half H8500/H9500 flat panel PMT. The readout of the scintillation array is obtained by coupling the scintillation array 104 to the photodetector array 108 via the slant fiberoptic light guide 106. With a sampling pitch of 5 mm, and the active size of each photodetector element of approximately 3 mm×3 mm, the average active surface coverage is about 35%.

A critical and integral part of the breast imager of the present invention is the data acquisition system accepting and digitizing signals from the readout system and then forwarding the digitized data to the computer system for data processing, data analysis, and tomographic image reconstruction. The readout system will depend on the particular choice of the technical solution selected for the imager modules.

In the first embodiment of a data acquisition and processing system according to the present invention, the breast PET imager has twelve detector modules arranged in a ring. Each module utilizes Hamamatsu H8500 flat panel PMT coupled to a pixelated LYSO scintillator array. Each PMT amplifier board provides four position-encoded analog signals and one analog sum signal for a total of 60 channels per detector. A trigger is formed in separate trigger hardware module. In the simplest form of the trigger circuitry, if any two of the twelve modules in the ring are in coincidence, the logic coincidence circuit will provide a single coincidence trigger to a data acquisition (DAQ) unit. Such function can be for example provided by a Mesytec MSCF-16 with its multiplicity trigger function which is available from Mesytec GmbH, Putzbrunn, Germany.

A preferred data acquisition system is the FPGA-based USB data acquisition system described in the articles "A flexible high-rate USB2 data acquisition system for PET and SPECT imaging" by Proffitt et al. in the 2005 IEEE Nuclear Science Symposium Conference Record, Puerto Rico, Oct. 23-29, 2005, pp. 2971-2975 and "Implementation of a High-Rate USB Data Acquisition System for PET and SPECT Imaging" by Proffitt et al. in the 2006 IEEE Nuclear Science Symposium Conference Record, San Diego, Calif., Oct. 29-Nov. 1, 2006, pp. 3063-3067, the entire contents of which are incorporated herein by reference thereto. The FPGA-based USB DAQ system has a modular, extensible architecture with up to 64 channels of simultaneous-sampling ADCs per unit and a sustained trigger rate of over 150 kHz for all 64 channels. In the case of a multi-ring (2-3 rings) system, each unit corresponds to one ring of modules. Each DAQ unit sends time-stamped raw event data over high-speed USB to its own acquisition computer. Each acquisition computer performs the centroid and energy calculations on all incoming data and sends this time-stamped processed data over gigabit Ethernet to the event builder/reconstruction computer. The event builder uses the time stamps to merge the separate detector events into a single coincident event. It may also perform image reconstruction or send the data to another computer for image reconstruction. The set of reconstructed tomographic images is sent to a user interface computer. Other readout systems with similar functionality are available commercially and can be used to achieve the same goals of recording and processing data from the proposed breast imager.

There are many variants of tomographic reconstruction software packages that are available commercially and can be used with the described here ring imager. The major function of detecting cancerous lesions across the whole breast volume, down to the base of the breast, can be achieved by using any of these available reconstruction algorithms described in the literature and/or available from software vendors.

As an example, a high resolution PET imaging module with a slant fiberoptic lightguide for improved detection efficiency for lesions located close to the chest wall of a patient was constructed according to the present invention. The prototype module was used to demonstrate experimentally the concept of implementing a fiberoptic slant light guide in a detector module. The prototype light guide was constructed of a glued regularly arranged tight array of 2 mm square-shaped double-clad polystyrene fibers which are available from Saint-Gobain Crystals of Hiram, Ohio. The parameters of the light guide included a 60.5 mm×62 mm surface, 56.5 mm length, 10 degree slant angle, and a resulting 12 mm side shift. The fiberoptic light guide transmitted light efficiently while preserving the geometrical relationships between pixels in the radiation sensor or scintillator. The other portions of this prototype module for a high resolution PET breast imager included a 50 mm×50 mm LYSO array of 2×2×10 mm pixels, available from Proteus of Chagrin Falls, Ohio and an H9500 flat panel PMT from Hamamatsu Corporation. Dry optical coupling was used on all optical surfaces. The high resolution PET breast imager module achieved a 12 mm shift of image which was sufficient to bypass or eliminate the dead edge of the detector module. This demonstrated the ability of the PET breast imager of the present invention to improved detection efficiency for lesions located close to the chest wall.

In the raw image obtained with the LYSO scintillation array, each scintillation pixel was very well separated. The energy spectrum was obtained from a single LYSO pixel when irradiated with a Na22 source. In the graphed energy spectrum, 511 keV and 1274 keV peaks were clearly visible. The energy resolution at 511 keV was 16% FWHM.

A comparison was obtained of the response with slant light guide removed and the LYSO scintillation array placed directly on top the H9500 flat panel PMT. In the raw image with the light guide removed, as expected the scintillation pixels were better separated than in the image taken with the light guide. In the energy spectrum obtained from a single LYSO pixel irradiated with a Na22 source, the energy signal on average was about two times higher than when the light guide was inserted. The energy resolution at 511 keV was 13% FWHM.

A comparison of the response with the slant light guide removed and the LYSO scintillation array placed directly on top the H9500 flat panel PMT showed that while the scintillation signal with the light guide in place is about ½ of the direct signal, the energy resolution performance remained very good, and the spatial resolution enabled operation with bright scintillators in the 1-3 mm pixel size. The results of this constructed first module for high resolution PET breast imager entirely confirmed the ability of the imager to improve detection efficiency of lesions located close to the chest wall of a patient. The scintillation signal detected at the level of the PMT was strong and provided very good spatial resolution and excellent energy performance.

Although the description above contains many specific descriptions, materials, and dimensions, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A breast imager for efficient detection of lesions located close to the chest wall of a patient comprising:
    a table for receiving a patient in the prone position, said table including a downward extending open tube for receiving the breast of the patient;
    one or more rings of gamma detection modules surrounding the breast in said tube;

each of said gamma detection modules including
a scintillator sensor adjacent said open tube;
an edge plane and a dead edge including a sharp drop in detection efficiency at said edge plane of said detection modules;
a slant imaging light guide extending from said scintillator sensor, said slant imaging light guide includes a slant angle between 5 and 45 degrees, said slant imaging light guide enables a side shift of image, said shift of image enabling elimination of said dead edge on one side of said detection modules;
a photo multiplier extending from said light guide; and
a readout connected to said photo multiplier;
a data acquisition system for accepting imaging data from said readouts of said gamma detection modules.

2. The breast imager of claim 1 wherein
said breast imager detects scintillation light produced by absorbed 511 keV gamma rays in the scintillator sensor; and
said breast imager includes a spatial resolution of 2 mm or better.

3. The breast imager of claim 1 wherein said one or more rings of gamma detection modules are capable of being scanned vertically toward and away from the chest wall of the patient to enable whole breast imaging.

4. The breast imager of claim 1 wherein
said breast imager includes three or more of said rings of gamma detection modules;
said rings of gamma detection modules are stationary with respect to said table; and
said stationary rings enable whole breast imaging of the breast with said gamma detection modules fixed in one position with respect to said table.

5. The breast imager of claim 1 wherein said gamma detection modules include
a scintillation module with an array of four round PMTs; and
a slant fiberoptic light guide coupled in a direct coupling mode between said scintillation module and said round PMTs.

6. The breast imager of claim 1 wherein said scintillator sensor is selected from the group including high stopping power plate crystal scintillator material and pixelated high stopping power crystal scintillator material.

7. The breast imager of claim 1 wherein
said scintillator sensor is constructed of pixelated high stopping power crystal scintillator material; and
said pixelated high stopping power crystal scintillator material is selected from the group including LSO, LYSO, LuAP, LFS, GSO, GYSO, BGO, NaI(Tl), and LaBr3.

8. The breast imager of claim 1 wherein
said ring is imbedded in said table to enable positioning the edge of said gamma detection modules directly at the chest wall; and
the geometry of said rings and said gamma detection modules significantly reduce dead regions in said breast imager.

9. The breast imager of claim 1 wherein said table is constructed of materials selected from the group including carbon fiber matrix, plastic, and lightweight metal.

10. The breast imager of claim 1 wherein said photomultiplier is selected from the group including a standard square photomultiplier, a standard round photomultiplier, a multi-element photomultiplier, a position sensitive flat panel photomultiplier, a position sensitive microchannel plate based photomultiplier, a large size avalanche photodiode with resistive readout, and a silicon photomultiplier array.

11. The breast imager of claim 1 wherein said slant imaging light guide material is selected from the group including glass, quartz, polystyrene, acrylic, polyvinyl toluene, and liquid core light guides contained in small diameter TEFLON® tubes.

12. The breast imager of claim 1 wherein
said slant imaging light guide includes an array of individual light guide elements; and
said light guide elements include a diameter or square profile of between 10 microns to 3 mm.

13. The breast imager of claim 1 wherein said photo multiplier is a compact silicon photomultiplier array.

14. The breast imager of claim 1 including
an optical window between said scintillation sensor and said light guide; and
said optical window enhances the transmission of light through said light guide.

15. The breast imager of claim 1 including an optical window between said light guide and said photo multiplier.

16. The breast imager of claim 1 wherein
said photomultiplier is an array of 3 mm×3 mm silicon photodetector units;
said silicon units are arranged into a 4×4 array of 16 units to form a basic buttable silicon PMT module; and
four of said basic buttable silicon PMT modules are arranged into a 2×2 array thereby forming a nominal 1" square photodetector.

17. A breast imager for efficient detection of lesions located close to the chest wall of a patient comprising:
a table for receiving a patient in the prone position, said table including a downward extending open tube for receiving the breast of the patient;
one or more rings of gamma detection modules surrounding the breast in said tube;
each of said gamma detection modules including
a scintillator sensor adjacent said open tube;
a slant imaging light guide extending from said scintillator sensor;
a photo multiplier extending from said light guide; and
a readout connected to said photo multiplier;
a data acquisition system for accepting in data from said readouts of said gamma detection modules;
said rings of gamma detection modules are divided into two or more ring sectors with each of said ring sectors including gamma detection modules thereon; and
said ring sectors including said gamma detection modules are rotated around the breast to provide more angular views for improved 3D tomographic reconstruction.

18. A breast imager for efficient detection of lesions located close to the chest wall of a patient comprising:
a table for receiving a patient in the prone position, said table including a downward extending open tube for receiving the breast of the patient;
one or more rings of gamma detection modules surrounding said open tube;
each of said gamma detection modules including
a scintillator sensor adjacent said open tube;
a slant imaging light guide extending from said scintillator sensor;
a photo multiplier extending from said light guide, said photo multiplier including an array of compact silicon photodetector units; and
a readout connected to said photo multiplier;

said one or more rings of gamma detection modules are scannable vertically toward and away from the chest wall of the patient;

said one or more rings of gamma detection modules are slightly rotatable around the breast in said tube; and a data acquisition system for accepting imaging data from said readouts of said gamma detection modules.

* * * * *